United States Patent [19]

Brown et al.

[11] Patent Number: 4,617,939

[45] Date of Patent: Oct. 21, 1986

[54] TOMOGRAPHY

[75] Inventors: Brian H. Brown; David C. Barber; Ian L. Freeston, all of Sheffield, England

[73] Assignee: The University of Sheffield, Sheffield, England

[21] Appl. No.: 745,291

[22] Filed: Jun. 14, 1985

Related U.S. Application Data

[63] Continuation of Ser. No. 489,415, Apr. 28, 1983.

[30] Foreign Application Priority Data

Apr. 30, 1982 [GB] United Kingdom ............... 8212676
Jun. 14, 1984 [GB] United Kingdom ............... 8415236

[51] Int. Cl.$^4$ ............................................. A61B 5/05
[52] U.S. Cl. .................................................. 128/734
[58] Field of Search ...................................... 128/734

[56] References Cited

U.S. PATENT DOCUMENTS 4,182,314  1/1980  Boughton ............................ 128/734
4,263,920  4/1981  Tatso et al. ........................ 128/734

OTHER PUBLICATIONS

Yamamoto et al, Med. & Biol. Eng. & Comput., vol. 17, Jan. 1979, pp. 135–137.

Primary Examiner—William E. Kamm
Assistant Examiner—John C. Hanley
Attorney, Agent, or Firm—King & Schickli

[57] ABSTRACT

Tomographic images ($I_1$ and $I_2$) of a body are constructed by placing a plurality of surface electrodes (1 to 16) at spaced intervals on the body (M), causing currents to flow in the body, and measuring the potential between pairs of electrodes, calculating the potential in each case on the assumption that the body consists of one uniform medium, plotting the isopotentials corresponding to the calculated results to create a uniform image of the body, obtaining the ratio between the measured potential and the calculated potential in each case, and modifying the image in accordance with the respective ratios by increasing the impedance along an isopotential in proportion to a ratio greater than unity or decreasing the impedance in proportion to a ratio less than unity. The calculations of potentials and the obtaining of ratios are carried out using a computer and the plotting of the isopotentials is carried out by a visual display unit (VDU) and/or a print-out unit run off the computer. An additional method is provided for indicating a change of state in the body. This method includes the step of determining ratios between initial and subsequent measured actual potentials between electrodes.

11 Claims, 16 Drawing Figures

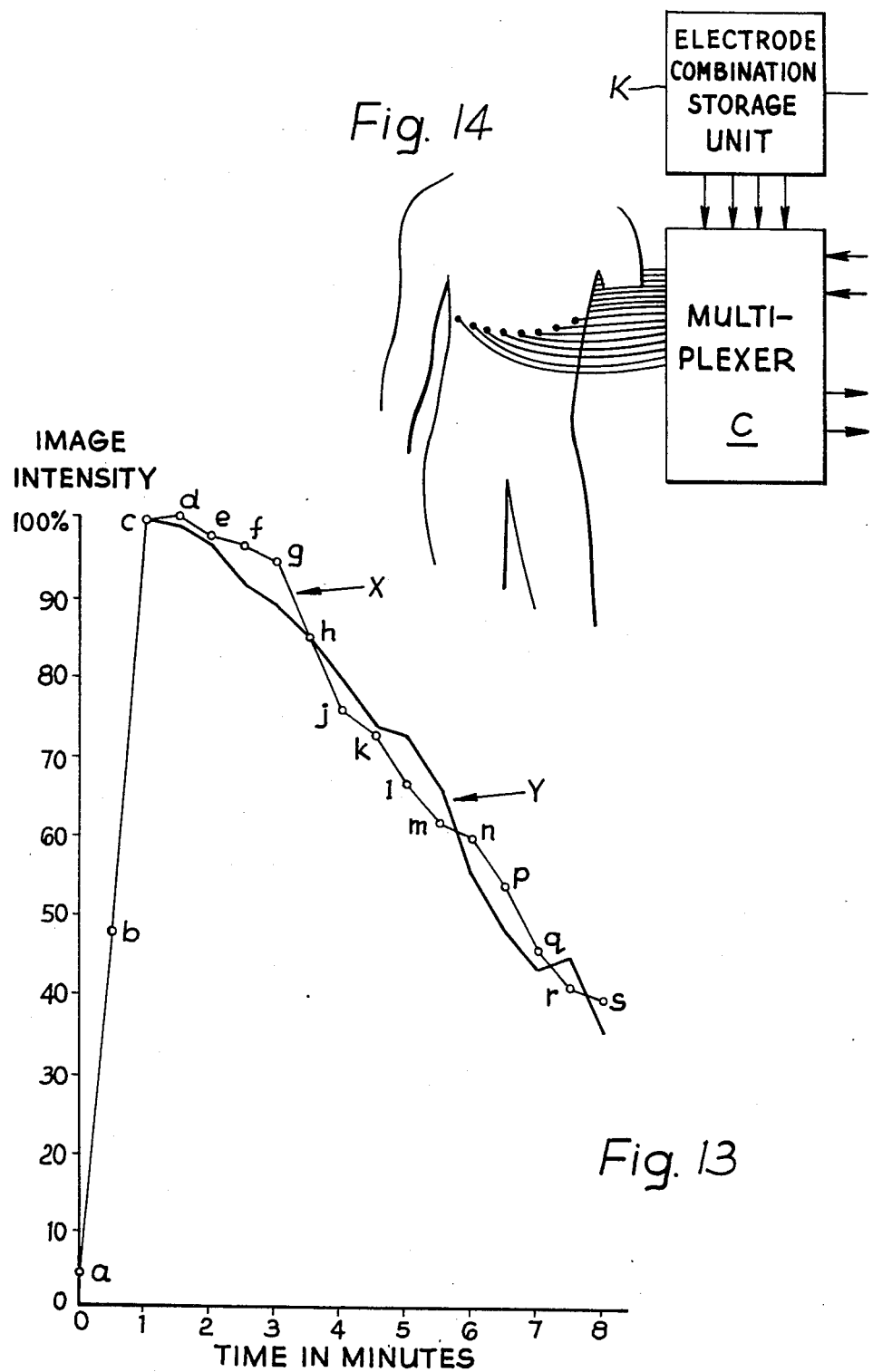

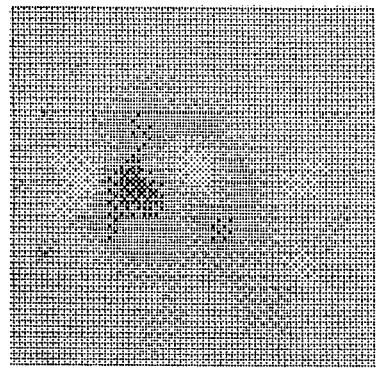
(a)
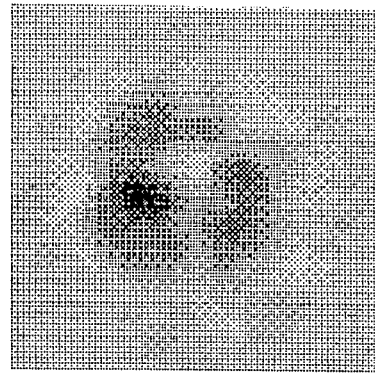
(b)
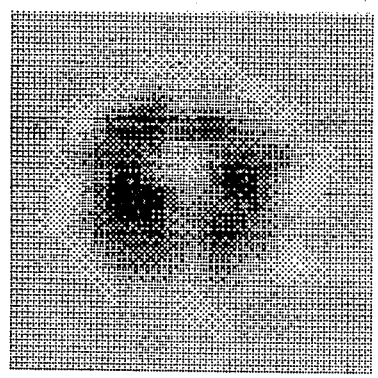
(c)
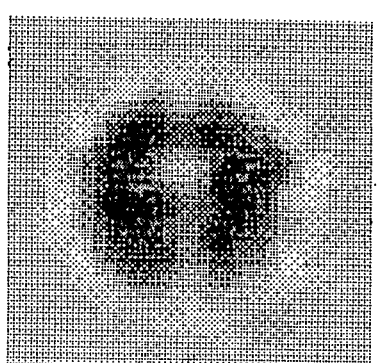
(d)
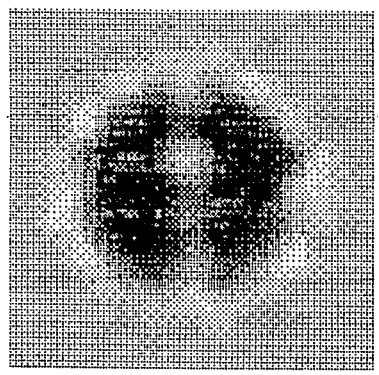
(e)
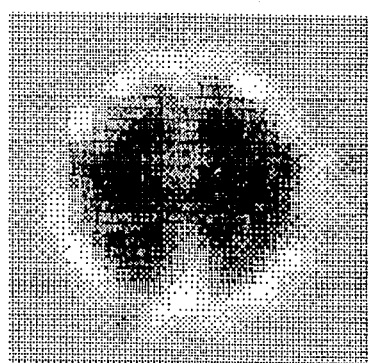
(f)
Fig. 15

TOMOGRAPHY

This is a continuation of application Ser. No. 489,415, filed Apr. 28, 1983.

TECHNICAL FIELD

This invention relates to tomography and has for its object the provision of a method of construction of tomographic images of a body or mass (hereinafter referred to simply as a body), more particularly—but not exclusively—of any part of a live human body.

BACKGROUND OF THE INVENTION

The success of X-ray computed tomography has encouraged the proposal of other medical imaging techniques not fraught with the dangers of X-rays. The use of low frequency electric currents has been suggested although no practical results have been published, but some literature exists on methods which involve measurements of impedance between electrodes on the surface of the body and propose methods for reconstruction of spatial impedance variations, for example, "An Impedance Camera for Spatially Specific Measurements of the Thorax" by R. P. Henderson and J. B. Webster (I.E.E.E. Trans on Biomed. Eng. Vol. 25, pp 250-254, 1978), "An Impedance Camera: A System for Determining the Spatial Variation of Electrical Conductivity" by R. J. Lytle and K. A. Dines (Lawrence Livermore Lab. Rep. U.C.R.L. 52413, 1978) and "Reconstruction of Spatial Resistivity Distribution of Conducting Objects from External Resistance Measurements by H. Schomberg (Philips GmbH, Hamburg, Mn MS-H, 1908V/78, 1978). Other examples include "Electrical Impedance Imaging of the Thorax" by Y. Kim, J. G. Webster and W. J. Tomkins (Jn. of Microwave power, 18(3), 245-257, 1983): "Fundamental study on electrical impedance CT algorithm utilising sensitivity theorem on impedance plethysmography", by K. Nakayama, W. Yagi and S. Yagi (Proc. of Vth (Int. Conf. on Electric Bio Impedance), Tokyo, 99-102, 1981): "A fundamental study of an electrical impedance CT algorithm", by K. Sakamoto and H. Kanai. (Proc. of VIth ICEBI, Zadar, Yugoslavia, 349-352, 1983): and "Methods and feasibility of estimating impedance distribution in the human torso", by Y. Yamashita and T. Takahashi. (Proc. of Vth ICEBI, Tokyo, 87-90, 1981). A current review is given by D. C. Barber and B. H. Brown (Applied Potential Tomography, Jn. of Physics E., 17,723-733, 1984). However, the resolution problem is much greater than that involved in X-ray computed tomography because the current flow in tissue is not confined to the direct path between a pair of electrodes. L. R. Price has suggested in "Imaging of the Electrical Conductivity and Permittivity Inside a Patient: A New Computed Tomography (CT) Technique" (Proc. Soc. Photo-Opt. Instrum. Eng. (USA), Vol. 206, pp 115-119, 1979) and "Electrical Impedance Computed Tomography (ICT): A New CT Imaging Technique" (I.E.E.E. Trans. Nucl. Sci., Vol. NS-26, pp 2736-2739, 1979) a method which forces a sinusoidal spatial potential function on the conducting medium such that the current paths are parallel streamlines. The ratio of current to applied voltage is thus dependent on the line integral of conductivity and so standard tomographic reconstruction procedures can be used. However, R. H. T. Bates, G. C. McKinnon and A. D. Seager have shown in "A Limitation on Systems for Imaging Electrical Conductivity Distributions" (I.E.E.E. Trans. on Biomed. Eng., Vol. 27, pp 418-420, 1980) that it is impossible to uniquely reconstruct images in this way unless ambiguities can be resolved by making extensive sets of measurements.

A major problem with any practical tissue resistance imaging method lies in the electrodes used to make contact. Electrode impedance is significant in comparison with tissue resistance at frequencies less than 100 kHz and operation at higher frequencies is extremely difficult because capacitive currents become significant. The impedance changes to be expected due to the spatial distribution of tissue resistivity are small and it is certainly necessary to be able to make measurements to an accuracy better than 1%. This is unlikely to be possible if electrode impedance is indistinguishable from tissue resistance.

SUMMARY OF THE PRESENT INVENTION

According to the present invention, a method for the construction of tomographic images of a body comprises placing a plurality of surface electrodes at spaced intervals on the body, causing currents to flow in the body, and measuring the actual potential between pairs of electrodes, calculating an assumed potential in each case on the assumption that the body consists of one uniform medium, plotting the isopotentials corresponding to the calculated results to create a uniform image of the body, obtaining the ratio between the measured actual potential and the calculated assumed potential in each case, and modifying the image in accordance with the respective ratios by increasing the impedance along an isopotential in proportion to a ratio greater than unity or decreasing the impedance in proportion to a ratio less than unity.

The modifying of the impedance distribution in this manner is known as "back projection", and the execution of the back projection (or the superimposition of the modified impedance along isopotentials) results in a tomographic image of the distribution of impedance over the cross-sectional area of the body in the plane containing the electrodes. The technique of back projecting is well known and widely used in x-ray tomography. A further explanation of back projecting may be found in the article entitled "Applied Potential Tomography" cited above and incorporated herein by reference.

At low frequencies the impedances within the body may be purely resistive, because displacement currents are negligible in this situation, in which case the image is of resistivity rather than impedance, and-therefore-references in the foregoing and hereafter to "impedance" in relation to the body are to be regarded as embracing the alternative of "resistivity" at the appropriate frequences.

Currents may be caused to flow in the body either by applying an electrical potential between each pair of electrodes in turn or by electromagnetic induction.

The invention makes use of the fact that, whilst it is difficult to make an accurate direct measurement of resistance, it is possible to make precise measurements of potential via an electrode as long as the electrode impedance is very much smaller than the input impedance of the recorder.

The resolution of the tomographic image may be improved by the well known technique of iteration. This involves recalculating the potentials in each case using the modified impedance distribution as an approximate guide to the actual distribution of impedance, obtaining the ratio between the recalculated potential and the measured potential in each case, and modifying the modified impedance distribution accordingly. Alternatively, an image filter can be applied to correct for the point response function at all points within the back projected image. Further, resolution may be enhanced by "weighting" the back projection ratios in accordance with the changing distribution of isopotentials through the body. Of course, it should be recognized that the techniques of iteration and weighting may be used together or separately.

The calculations of potentials and the obtaining of ratios may be carried out using a computer programmed with standard software readily available on the market. The plotting of the isopotentials is carried out by a visual display unit (VDU) and/or a print-out unit run off the computer. Alternatively, the above calculations, iterations, filtering, and weighting can be performed by electronic circuits specific for this purpose rather than by numerical calculations using an electronic computer.

Where it is desired to study rapid changes in the internal state of the body, a slightly modified monitoring method is required. The modified monitoring method includes the steps of placing an array of spaced electrodes in contact with the body, causing currents to flow in the body, by applying an electrical potential between pairs of electrodes in turn, calculating the potentials between other pairs of electrodes on the assumption that the body consists of one uniform medium, plotting the isopotentials corresponding to the calculated results to create an assumed image of the body, measuring initial potentials between those other pairs of electrodes in sequence over the array of electrodes, measuring subsequent potentials between the same pairs of electrodes in the sequence after a change in the internal state of the body, determining the ratios between the initial potentials and the subsequent potentials in each case and modifying the image by back projecting the respective ratios along the appropriate isopotentials and thereby increasing the impedance along an isopotential in proportion to a ratio greater than unity or decreasing the impedance in proportion to a ratio less than unity.

The image produced by this method does not contain the static structures within the body but gives a picture of the internal state of the body after the change of state, which may be effected by means of an injection into the blood stream and/or by ingesting food and/or drink, or which may be the result of respiration, gastric emptying, internal bleeding, or the cardial cycle, and the plotting of the image may be effected by a visual display unit (VDU) and/or a printout unit, forming images by intensity of dots in proportion to impedance.

The modified method of the present invention is particularly advantageous in being able to afford a "dynamic" picture of the continually changing state within a body by repeating the potential measuring sequence and potential difference determinations at regular and/or frequent intervals, and recording and/or viewing the successive modified images corresponding thereto. Changes in impedance distribution can be seen even in the presence of very much larger static impedance variations.

A rate of change of state within the body may be obtained by plotting a graph of the intensity of dots corresponding to the organ under investigation.

BRIEF DESCRIPTION OF THE DRAWING

One method of carrying out the invention and modifications thereof will now be described, by way of example only, with reference to the accompanying drawings, in which:

FIG. 13 shows a graph depicting the gastric emptying rate corresponding to the sequence of print-outs of FIG. 12, with a corresponding graph derived from gamma camera pictures of the same stomach during the emptying cycle;

FIG. 14 corresponds to the left hand end of FIG. 10 but shows the electrode array round the torso of the human body.

FIG. 15 is a sequence of print-outs at intervals of 1 second with the arrangement of FIGS. 10 and 11 as modified by FIG. 14 during the respiration cycle.

DETAILED DESCRIPTION OF THE INVENTION

Figure 1:
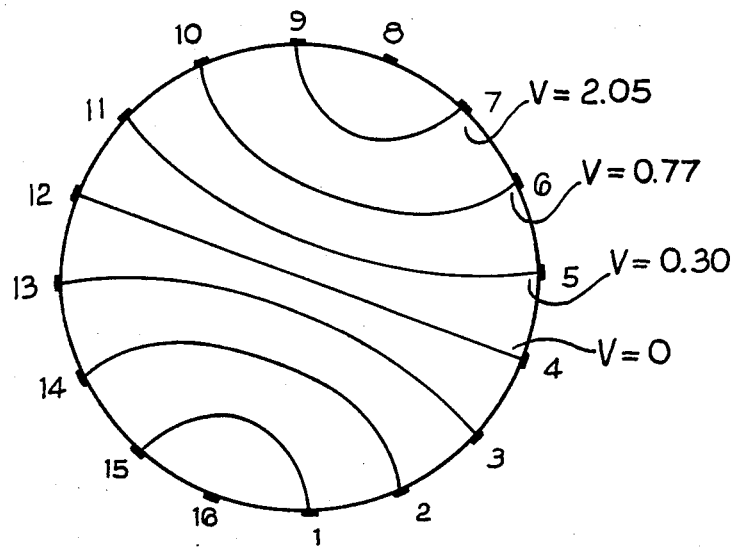
FIG. 1 is a diagram of an example using an array of sixteen surface electrodes equi-spaced round a body.
Figure 5:
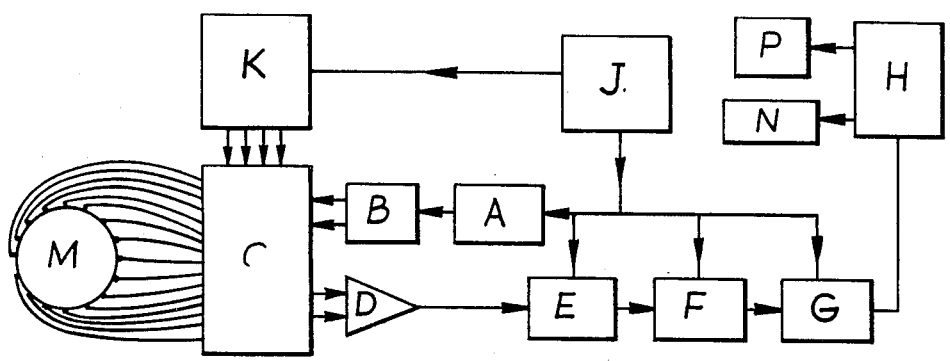
FIG. 5 is a block circuit diagram of equipment used in conjunction with the electrode array of FIG. 1 to produce the tomographic images of FIGS. 2 and 3.

Referring to FIGS. 1 and 5, an applied potential of approximately 3 volts at 4 milliamps is produced by a waveform generator A at 50 kHz and applied through a voltage to current converter B and a multiplexer C in turn between every electrode combination and in each and every case the resultant potential between every adjacent pair of electrodes is fed through an amplifier D and a phase sensitive detector E and is recorded by a sample and hold unit F, from which the data is fed through a 12-Bit analogue to digital converter G to a computer H. The units A, E, F and G of the equipment are all controlled by a master clock J, which also controls the multiplexer through a unit K which stores the electrode combinations. The sixteen electrodes shown in FIG. 1 give rise to 1456 potential measurements which can be recorded in 1.456 seconds or less.

Figure 16:
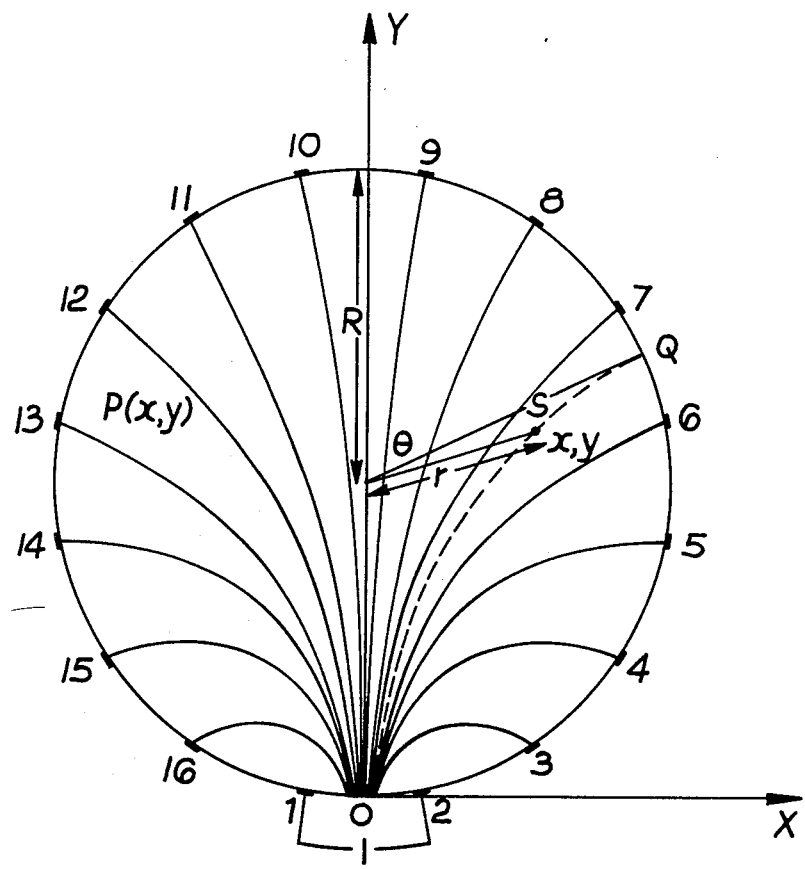
FIG. 16 is a diagrammatical representation for reference in explaining back projecting.

In order to demonstrate image reconstruction it is necessary to consider a specific configuration of electrodes on a specific object (see FIG. 16). The object chosen for illustration is a thin flat sheet of electrically resistive material enclosed by a circular boundary. Connected to the boundary of this object are a number of equally spaced electrodes. For example, 16 electrodes may be attached to the boundary. Let these electrodes be numbered from 1 to 16. Then current is passed between electodes 1 and 2 (see FIG. 16) and the voltages between electrodes 3 and 4, 4 and 5 and so on up to 15 and 16 are measured by the apparatus. Although ideally the voltages between the electrode pairs (16,1), (1,2) and (2,3) should also be measured their values are distorted by the presence of a voltage drop across these electrodes due to the electrode contact resistance. The other measurements e.g. between electrodes 3 and 4 can be made without taking any current through these electrodes and so this problem does not occur for these measurements, which is an important feature of this technique.

Once the measurements have been made for current passing between electrodes 1 and 2, current is then directed to the apparatus to flow between electrodes 2 and 3 and a second set of measurements taken. This process is continued until finally current is passed between electrodes 16 and 1. When this final set of measurements is complete a full set of 16 sets of measurements is available for reconstruction of an image of resistance distribution in the object.

The distribution of voltage within an object through which electric current is flowing is determined by the equation (Eq 1).

$$\nabla^2 V = \nabla P \cdot \nabla V \quad (1)$$

where $\rho(x,y,z)$ is the distribution of log resistance in the object i.e. if the resistance at a point is $\rho(x,y,z)$ then $P = IN (\rho)$ where ln is the natural logarithm function. This formula will give the value of voltage at the object boundary or surface of and the primary assumption behind resistance imaging is that if enough different independent current patterns are applied to the object and enough boundary measurements of voltage made the distribution of P can be determined. Other methods of attempting to solve this problem require the accurate and repeated solution of the above equation for the object being probed. This, except for the most trivial examples, is a formidable task and effectively prevents the use of these techniques with currently available computing equipment. Such a calculation would also need detailed information about the object boundary which would be difficult to obtain without extensive and elaborate additional instrumentation. In contrast the method presented here does not require explicit solution of the above equation either once or repeatedly in an iterative cycle and is able to produce (and has produced) in-vivo images of resistance distribution in times of no more than a few tens of seconds.

The present method may in fact be formulated for a general three dimensional object. However because the reconstruction of the image does not require the solution of Eq. 1 it has been shown experimentally that good images using data obtained from three dimensional objects may be obtained by applying an algorithm designed for a simple two dimensional configuration. The formulae given below refer to the idealized case of a two dimensional distribution of resistance enclosed by a circular boundary and with a pair of drive electrodes very close together, effectively forming a current dipole.

FIG. 16 represents such an idealized region with 16 electrodes placed at equal intervals around the boundary and with a current dipole at the origin 0. In practice current would actually be passed between electrodes 1 and 2 in this example but the differences in the pattern of current flow between this latter configuration and the current dipole are negligible except close to the drive electrodes.

In the example given above passing current between a pair of electrodes (called hereafter the drive pair) enables 16 measurements of voltage difference to be made around the boundary of the object. In practice only 13 measurements can be made because measurements involving one of the drive electrodes are unreliable because of contact resistance. The missing values can be interpolated from the available measurements. Let this set of measurements be described by a vector v. If the current is being passed between electrodes i and i+1 this vector will be called $v_i$.

Let the natural logarithm of the resistance distribution within the region enclosed by the circular boundary be given by P(x,y) (FIG. 16). The algorithm being described here initially reconstructs an image of P(x,y) which may then be converted to an image of resistance (x,y) by the operation of exponentiation. Consider current being passed by a current dipole at 0. A vector of measurements $\overline{v}_1$ is obtained. Now suppose that the resistance in the region is set to some uniform value. Again current is passed between electrodes 1 and 2 and this time a vector of measurements $\overline{u}_1$ is obtained. A new vector $\overline{P1} = (\overline{v}_1 - \overline{u}_1)/\overline{u}_1$ is formed and this is back-projected into the image space along the lines of constant potential. These lines are shown in FIG. 16 and represent the lines of constant voltage in the medium when current is flowing through the medium. For the configuration shown in FIG. 16 the lines of constant voltage are given by the points for which $$V = \frac{m x}{x^2 + y^2} \quad (2)$$

is constant where m is the strength of the current dipole.

By back-projection the following is meant. Consider an image point S at (x,y), initially with value zero. The equipotential passing through it when continued to the boundary intersects at a point Q which is generally between two electrodes. The intersection point on the boundary (see FIG. 16) is given by $$0 = 2 \cdot \tan^{-1}\left(\frac{2Rx}{x^2 + y^2}\right) \quad (3)$$

The boundary value of $\overline{p}$ at this point is then assigned to the image point at x,y. This process is repeated for all image points inside the boundary. The resulting image is called a single back-projection of the vector $\overline{p}$.

A back projection image is produced for each of the data vectors $\overline{p1}$. x and y in the above equations are local coordinates relative to an origin at the current dipole. For 16 electrodes there would be 16 such back projection images. These are then added together in a weighted manner. Consider the point x,y in FIG. 16. For each back projection the value of the back projection image at the point x,y is multiplied by the weighting term $$\left(\frac{y}{x^2+y^2} - \frac{1}{2R}\right)\left(1 - \frac{r^2}{R^2}\right) \quad (4a)$$

if uniform sensitivity to spaced objects is required or by $$\frac{y}{x^2+y^2} - \frac{1}{2R} \quad (4b)$$

if uniform sensitivity to a distributed change in resistance is required and the modified value restored to the image. When all 16 images have been modified in this way each image is converted to an absolute coordinate system by rotation about the centre of the image circle. For the ith image the angle of rotation is $(i-1)2\pi/16$ radians. They are then added together to produce an image representing the distribution of resistance in the object being imaged.

The image produced in this way is still a blurred representation of the original object. If a very fine point-like object were being imaged the image would be a blurred representation of the object with a second central moment given by d. d must be measured experimentally. The amount of blurring is a function of the distance from the centre of the object. If the amount of blurring at the centre is given by $d_0$ then the amount of blurring at a distance r from the centre is $$d = d_0\left(1 - \frac{r^2}{R^2}\right) \quad (5)$$

In order to reduce this blurring as far as possible a filtering process is applied to the image. An image may be partially deblurred by subtracting the Laplacean filtered image from the original image. If the image is f(x,y) then the deblurred image is given by $$g(x,y) = f(x,y) - d^2 \cdot \bar{\nabla}^2 f(x,y) \quad (6)$$

where $$\bar{\nabla}^2 = \underline{d} + d$$

$$dx^2 dy^2$$

From equation 5 it is seen that d is a function of the distance from the centre of the image. Alternatively the image can be radially distorted to an image in which the value of the distorted image at a distance s from the centre of the image is given by the value at a distance r from the centre of the undistorted image where $$r = R \cdot \tanh s \quad (7)$$

After this distortion the blurring is uniform across the image and the Laplacian filter can be applied with $d = d_0$. Finally the distorted image is restored using the radial transform $$s = 0.5 \ln \frac{1 + r/R}{1 - r/R} \quad (8)$$

The formulae given above apply to the case of a two dimensional object enclosed within a circular boundary and with current applied by a current dipole. Similar but more complex formulae exist for finitely spaced electrodes but for two dimensional objects of more general boundary shape no simple analytic forms exist, although values for the weights and equipotentials may be computed numerically. For three dimensional objects no simple closed analytic forms exist, even for most regular boundary shapes. However, useful images may be produced by assuming all problems are of the two dimensional form. Provided that data is collectd using electrodes situated on the intersection of a plane through the object and the boundary of the object and that values of $u_i$ are known the vectors p may be back-projected using the formulae given above to produce images.

It should also be appreciated that the $\bar{u}_i$ may be obtained in practice by using a tank of conducting fluid with electrodes connected to the boundary of this tank and measuring the $\bar{v}_i$ with the object immersed in the tank and the $\bar{u}_i$ with the object removed and replaced by conducting fluid. Finally if changes in resistance are all that is required measurements of $\bar{v}_i$ measured before the changes occur may be substituted for the $\bar{u}_i$; in this case the images represent changes in resistance, such as those associated with physiological changes in the body. In this case direct connection to the body can be made.

FIG. 1 also shows the isopotentials to be expected when current is applied between electrodes 8 and 16 adjacent the surface on a body L assumed to consist of one uniform medium. In FIG. 5 the sixteen electrodes are to be considered as being equi-spaced around a human arm M at the cross-section shown in FIG. 4. The recorded potentials are compared by the computer H with the respective calculated potentials and the ratios are back projected along the appropriate isopotentially as described in detail above. Thus twelve or thirteen back projections can be made for every pair of current drive electrodes (a potential cannot be recorded from a current drive electrode) and the modified isopotentials plotted. The plots of the modified impedance along isopotentials are superimposed on those obtained for each and every pair of drive electrodes, by means of the computer linked to a print-out N, to give a tomographic image $I_1$ as in FIG. 2, and to a visual display unit (VDU) P, to give a visually displayed image $I_2$ as in FIG. 3.

Figure 2:
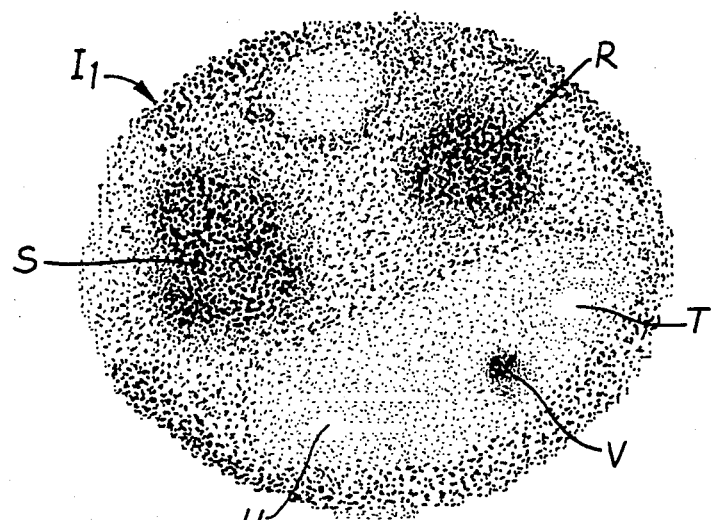
FIG. 2 is a print-out tomographic image of one cross-section of a human arm using the electrode array of FIG. 1.
Figure 3:
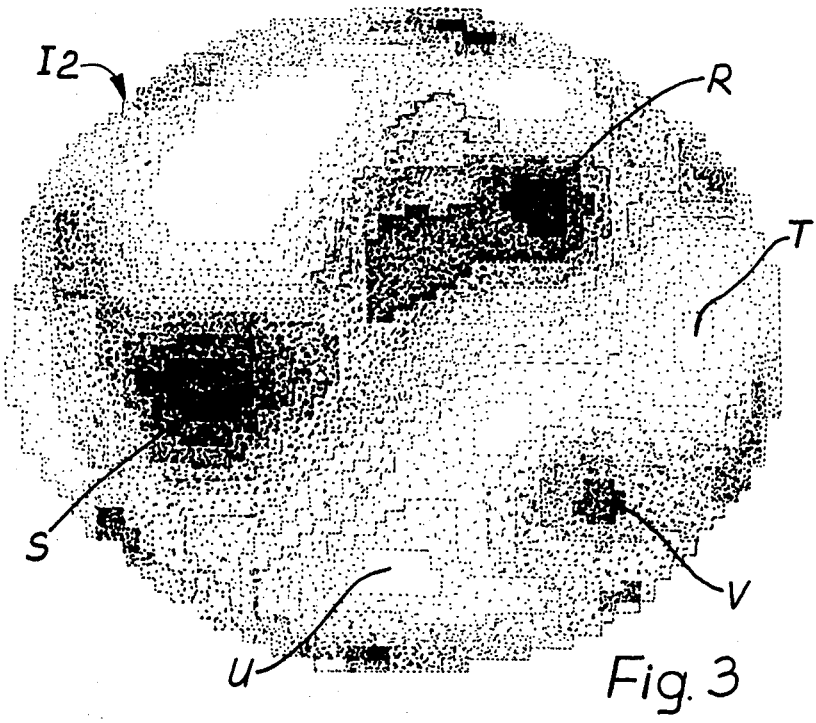
FIG. 3 is the corresponding image on a visual display unit (VDU)
Figure 4:
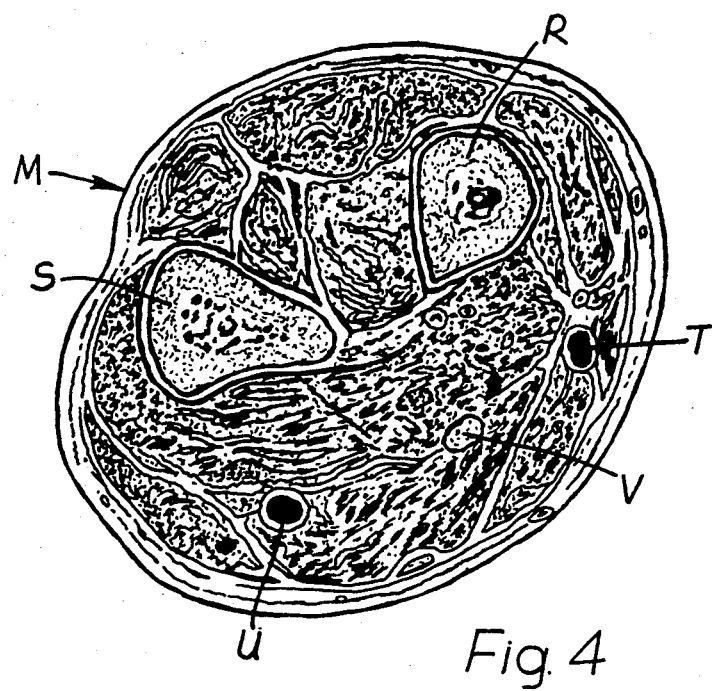
FIG. 4 is the corresponding actual cross-section of the human arm.

Comparing FIGS. 2, 3 and 4 it is possible to identify in the images $I_1$ and $I_2$ the radius and ulna bones R, S respectively, the radial and ulna arteries T, U respectively, and the median nerve V. With greater resolution of the images more constituent parts of the arm M could be identified.

In addition to improving the resolution by iteration, the resolution can also be improved by increasing the number of electrodes to say 32, but this will call for more elaborate computing equipment to handle the increased number of recordings and calculations.

Figure 6:
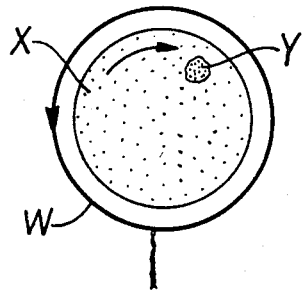
FIGS. 6 and 7 are diagrams illustrating two ways of inducing currents in a body.
Figure 7:
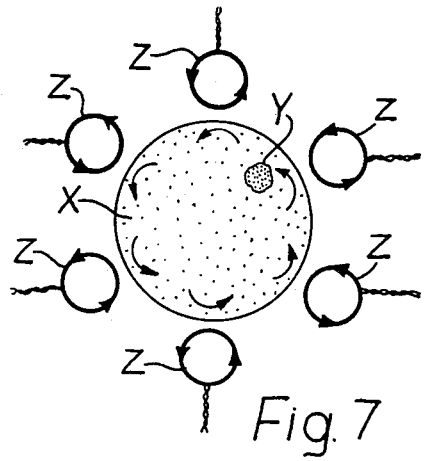

In FIG. 6 a coil W electromagnetically induces a current in a body X and an inhomogeneity Y causes surface potentials to be induced and which can be picked up by electrodes disposed as in FIG. 1 and processed by modified equipment as in FIG. 5, while in FIG. 7 currents are induced by a plurality of coils Z equi-spaced around the body X.

Figure 8:
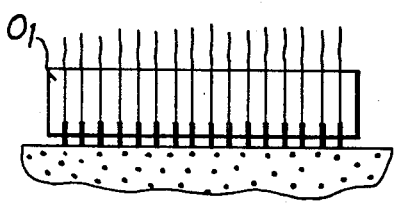
FIGS. 8 and 9 are diagrams illustrating respectively a linear array of electrodes in a block, and the use of blocks of contoured arrays of electrodes.
Figure 9:
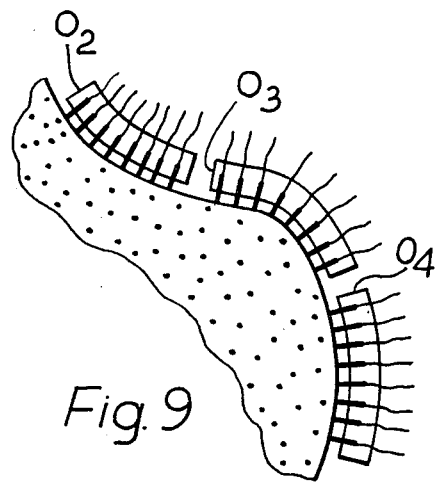

In FIG. 8 a linear array of electrodes is mounted in a block $0_1$, while in FIG. 9 blocks $0_2$, $0_3$, $0_4$ of contoured arrays of electrodes correspond to parts of the contour of a body.

The method of the invention can also be applied to tomographic image construction from three-dimensional data, but this involves taking into account the spread of current out of the plane of the electrodes and either back projection has to be made over isopotential surfaces, or the three-dimensional data reduced to two-dimensional format, which—again—calls for more elaborate computing equipment.

A slightly modified method for monitoring a change in the internal state of the body will now be described in detail.

Figure 10:
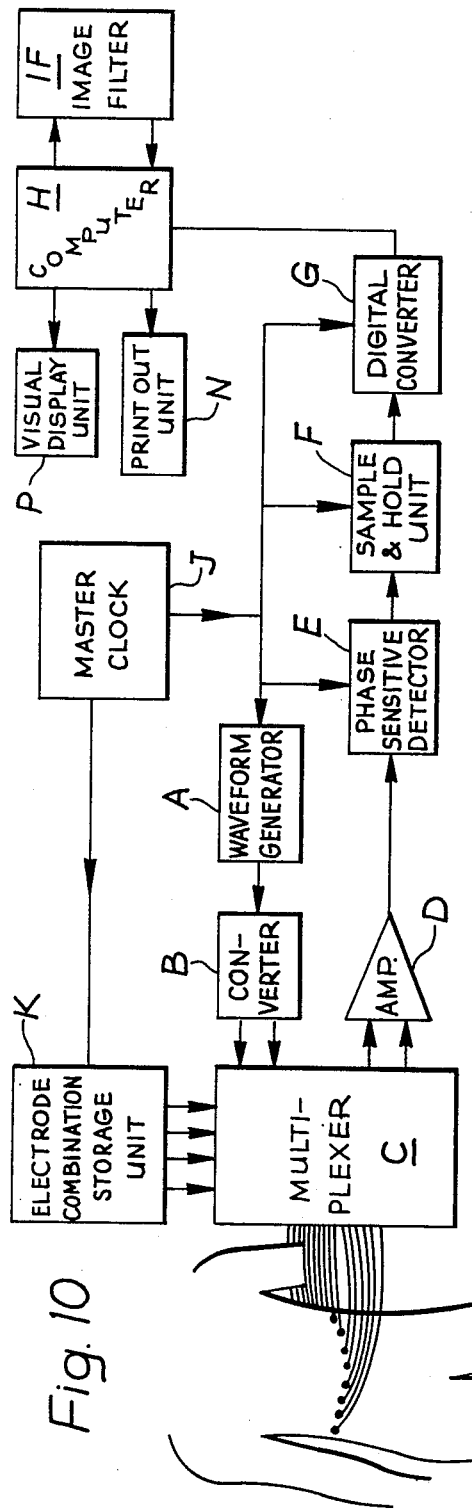
FIG. 10 is a block circuit diagram of equipment as shown in FIG. 5 used in conjunction with an electrode array as shown in FIG. 1 but indicated diagrammatically round the abdomen of a human body.
Figure 11:
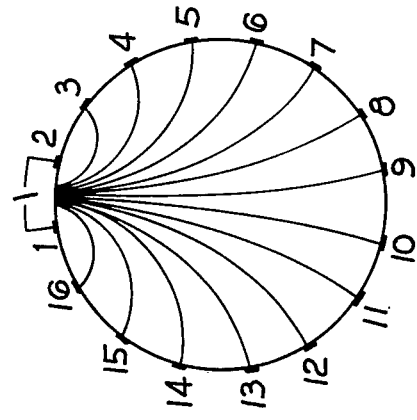
FIG. 11 is a diagrammatic plan of the electrode array of FIG. 10.

Referring to FIGS. 10 and 11, an array of sixteen Ag/AgCl electrodes equi-spaced round the abdomen of a human body is coupled to equipment substantially as described above and shown in FIG. 5. FIG. 11 shows the assumed image of isopotentials to be expected when current is applied between electrodes 1 and 2, with the body assumed to consist of one uniform medium and circular in cross-section.

Figure 12:
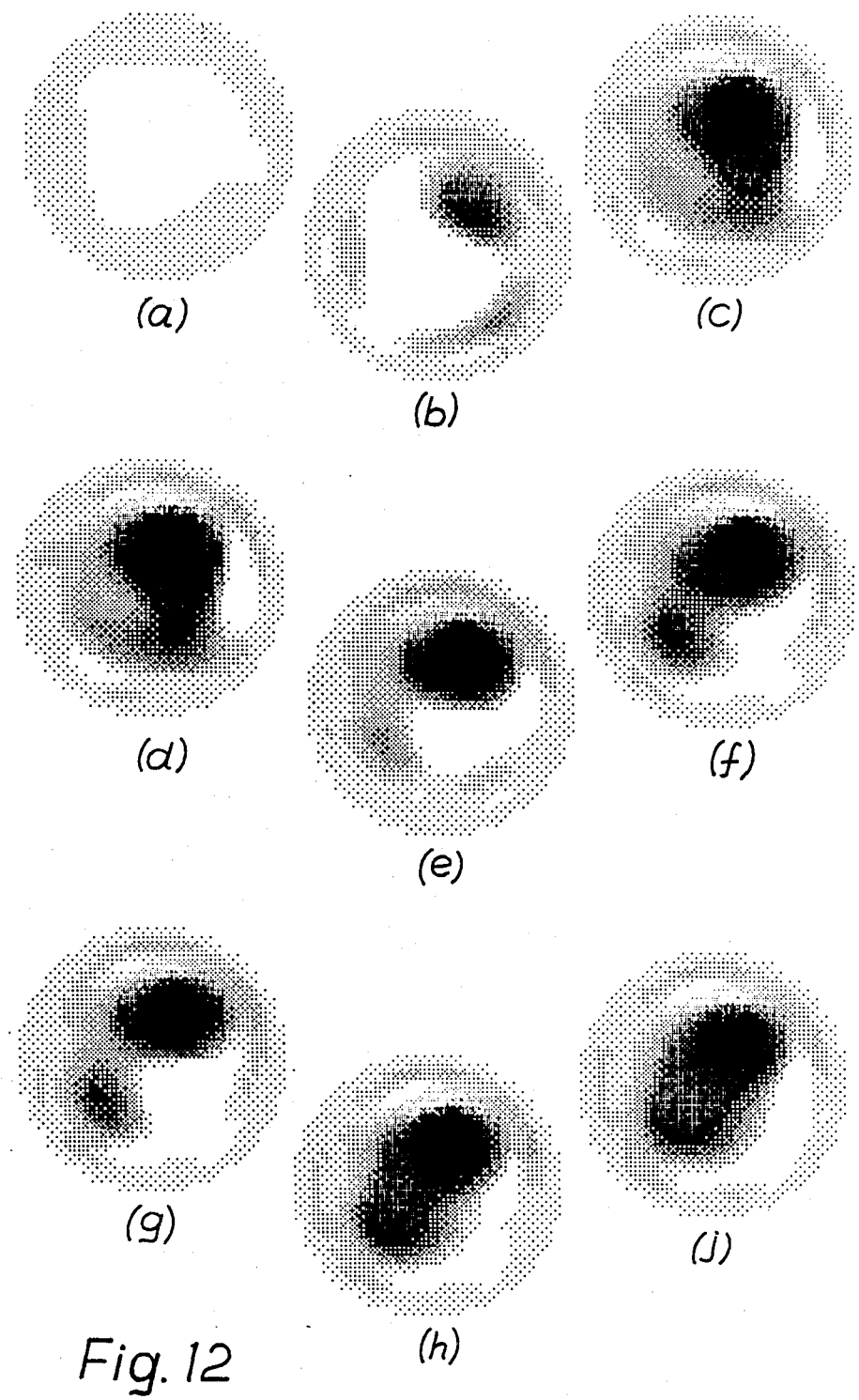
FIG. 12 is a sequence of print-outs at intervals of 30 seconds with the arrangement of FIGS. 10 and 11, drink of 300 ml of tap water being taken before print-out (b)
Figure 12:
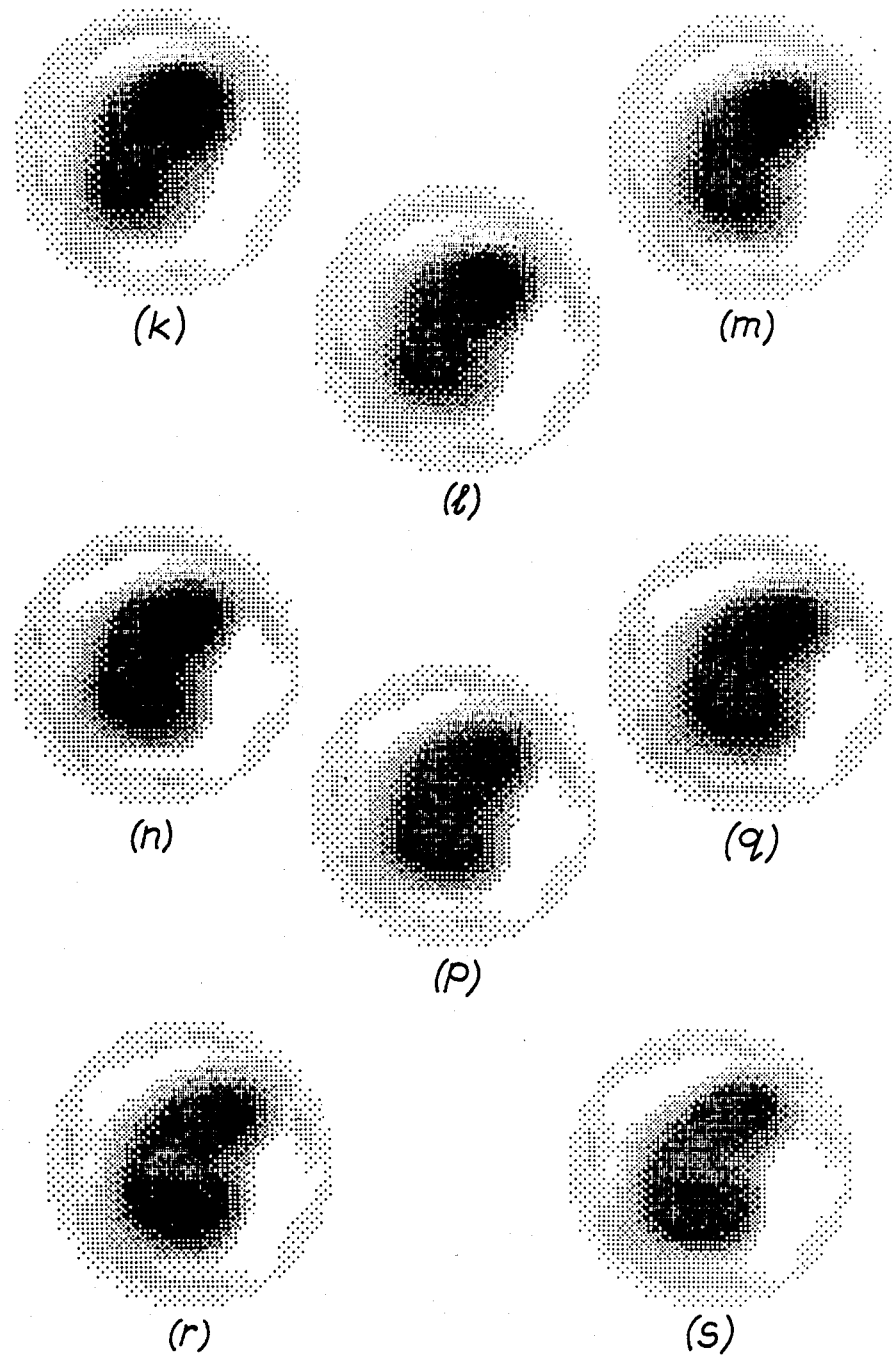

Initial potentials between adjacent pairs of electrodes (other than the pair between which the current is applied) are measured in sequence over the array of electrodes, subsequent potentials between the same pairs of electrodes are measured in the same sequence after a change in the internal state of the body (which in this case results from having a drink—as indicated previously and as will be referred to again presently with reference to FIGS. 12 and 13), the subsequent potentials are compared by the computer H with the respective initial potentials, and the ratios are back projected along the appropriate isopotentials shown in FIG. 11, by increasing the impedance along an isopotential in proportion to a ratio greater than unity or decreasing the impedance in proportion to a ratio less than unity. Thus thirteen back projections can be made for every pair of current drive electrodes (a potential cannot be recorded from a current drive electrode) and the modified impedances along the isopotentials plotted just as described above. The plots of the modified impedance along isopotentials are superimposed on those obtained for each and every pair of drive electrodes, by means of the computer linked to a print-out N, to give a back projected tomographic image of the type shown in FIG. 12, and to a visual display unit (VDU) P, to give a visually displayed back projected image (not shown).

In FIG. 12 the stomach is well outlined following the drink, which is taken before print-out (b). Anterior is on the right and left is at the top of each image. As the changes disappear in the stomach they appear in the small intestine. By taking the maximum intensity of image in FIG. 12 as 100% it is possible to plot a graph X in FIG. 13 showing gastric emptying, which compares with a corresponding graph Y derived from gamma camera pictures of the same stomach during the emptying cycle; but it must be borne in mind that in the latter case the subject or patient has to suffer the discomfort and risk of a radioactive meal in order for the gamma camera pictures to be taken.

In FIG. 14 the sixteen electrodes are disposed round the torso, and FIG. 15 shows a resulting sequence of six print-outs at intervals of 1 second during inspiration after inhalation respectively of (a) 0.45, (b) 1.0, (c) 1.5, (d) 2.0, (e) 2.7 and (f) 4.2 liters of air. The lungs are clearly seen, with anterior at the bottom of each image. Any defect in ventilation will show as a direction of the image of the lungs.

What we claim is:

1. A method for the construction of tomographic images of a body comprising placing a plurality of electrodes adjacent the skin at spaced intervals on the body, causing currents to flow in the body by applying an electrical potential between pairs of electrodes in turn, and measuring potentials between other pairs of electrodes, calculating potentials for each electrode pair on an assumption that the body consists of one uniform medium, plotting isopotentials corresponding to the calculated potentials to create an assumed image of the body, obtaining a ratio between the measured potential and the calculated potential for each electrode pair, and modifying the assumed image by back projecting respective ratios for each electrode pair along the plotted isopotentials and thereby increasing impedance along each plotted isopotential in proportion to a ratio greater than unity or decreasing the impedance in proportion to a ratio less than unity.

2. A method as in claim 1, including the additional step of applying an image filter to improve tomographic image resolution.

3. A method as in claim 1, wherein said steps of calculating potentials and obtaining ratios is carried out using a computer and the step of plotting isopotentials is carried out by a visual display unit.

4. A method as in claim 1 wherein said steps of calculating potentials and obtaining ratios is carried out using a computer and the step of plotting isopotentials is carried out by a print-out unit run off the computer.

5. A method as in claim 1, including the additional step of mounting a linear array of electrodes in a block.

6. A method as in claim 5, including the additional step of contouring said block to correspond to parts of the contour of the body.

7. A method for the construction of tomographic images of a body comprising placing an array of spaced electrodes in contact with the body, causing currents to flow in the body by applying an electrical potential between pairs of electrodes in turn, calculating potentials between other pairs of electrodes on an assumption that the body consists of one uniform medium, plotting isopotentials corresponding to the calculated potentials to create an assumed image of the body, measuring initial potentials between those other pairs of electrodes in sequence over the array of electrodes, measuring subsequent potentials between the same other pairs of electrodes in the sequence after a change in the internal state of the body, determining ratios between the initial potentials and the subsequent potentials for each other pair of electrodes, and modifying the assumed image by back projecting the respective ratios for each other pair of electrodes along the plotted isopotentials and thereby increasing impedance along each plotted isopotential in proportion to a ratio greater than unity or decreasing the impedance in proportion to a ratio less than unity.

8. A method as in claim 7, wherein the plotting of the image is effected by a visual display unit.

9. A method as in claim 7, wherein the plotting of the image is effected by a print-out unit forming images by intensity of dots in proportion to impedance.

10. A method as in claim 9 wherein a rate of change of state within the body is obtained by plotting a graph of the intensity of dots corresponding to the organ under investigation.

11. A method as in claim 7 wherein a "dynamic" picture of the continually changing state within the body is provided by repeating the potential measuring and ratio determining steps at intervals and plotting the successively modified images corresponding thereto.

* * * * *